United States Patent [19]
Pretzer et al.

[11] 4,339,608
[45] Jul. 13, 1982

[54] PROCESS FOR SELECTIVE FORMATION OF $C_4$ COMPOUNDS AND TERTIARY ORGANO GROUP VA COMPOUND-CONTAINING CATALYST SYSTEM USED THEREIN

[75] Inventors: Wayne R. Pretzer; Thaddeus P. Kobylinski; John E. Bozik, all of Gibsonia, Pa.

[73] Assignee: Gulf Research & Development Company, Pittsburgh, Pa.

[21] Appl. No.: 215,354

[22] Filed: Dec. 11, 1980

Related U.S. Application Data

[63] Continuation-in-part of Ser. No. 42,330, May 25, 1979, which is a continuation-in-part of Ser. No. 957,130, Nov. 2, 1978, and Ser. No. 936,717, Aug. 25, 1978.

[51] Int. Cl.³ .................. C07C 27/22; C07C 45/50
[52] U.S. Cl. .................. 568/487; 568/888; 568/902
[58] Field of Search ............... 568/902, 888, 905, 487

[56] References Cited
U.S. PATENT DOCUMENTS

| | | | |
|---|---|---|---|
| 2,623,906 | 12/1952 | Gresham | 260/615 |
| 3,248,432 | 4/1966 | Riley et al. | 260/638 |
| 3,285,948 | 11/1966 | Butter | 260/642 |
| 3,387,043 | 6/1968 | Kurasihi et al. | 568/902 |
| 4,133,966 | 1/1979 | Pretzer et al. | 568/902 |
| 4,168,391 | 9/1979 | Slinkard et al. | 568/902 |
| 4,171,461 | 10/1979 | Bartish | 568/902 |
| 4,190,729 | 2/1980 | Forster | 568/487 |
| 4,205,190 | 5/1980 | Gane et al. | 568/902 |
| 4,262,154 | 4/1981 | Gane et al. | 568/902 |

Primary Examiner—Werren B. Lone
Attorney, Agent, or Firm—Deane E. Keith; Forrest D. Stine; Joseph J. Carducci

[57] ABSTRACT

A process and catalyst system for selectively producing n-butanol and n-butanal which process comprises introducing into a reaction zone methanol, hydrogen, carbon monoxide and a catalyst system consisting essentially of (a) a cobalt carbonyl, a hydrido cobalt carbonyl or a cobalt-containing material convertible to a cobalt carbonyl or a hydrido cobalt carbonyl, (b) an iodine compound and (c) a tertiary organo Group VA compound and then subjecting the contents of said reaction zone to an elevated temperature and an elevated pressure for a time sufficient to convert methanol to n-butanol and n-butanal.

26 Claims, No Drawings

PROCESS FOR SELECTIVE FORMATION OF C4 COMPOUNDS AND TERTIARY ORGANO GROUP VA COMPOUND-CONTAINING CATALYST SYSTEM USED THEREIN

CROSS-REFERENCES TO RELATED APPLICATIONS

This application is a continuation-in-part application of our U.S. patent application Ser. No. 42,330, filed May 25, 1979, entitled "Process for Producing Acetaldehyde," which, in turn, is a continuation-in-part application of U.S. patent application Ser. No. 957,130, filed Nov. 2, 1978, entitled "Critical I/Co Ratios for the Selective Production of Acetaldehyde in a Carbonylation Process" and of U.S. patent application Ser. No. 936,717, filed Aug. 25, 1978, entitled "A Process for Selective Formation of Acetaldehyde from Methanol, Hydrogen and Carbon Monoxide Using a Cobalt Source in Combination with an Arsenic or Antimony Base Ligand and an Iodine Promoter."

Reference is made to the following U.S. applications filed on even date:

U.S. patent application Ser. No. 215,556 to Wayne R. Pretzer, Thaddeus P. Koblyinski and John E. Bozik entitled "Selective Formation of C4 Compounds and Organic Sulfide-Containing Catalyst System Used Therein."

U.S. patent application Ser. No. 215,554 to Wayne R. Pretzer, Thaddeus P. Koblyinski and John E. Bozik entitled "Selective Formation of C4 Compounds and Bisphosphine Disulfide-Containing Catalyst System Used Therein."

U.S. patent application Ser. No. 215,555 to Wayne R. Pretzer, Thaddeus P. Koblyinski and John E. Bozik entitled "Selective Formation of C4 Compounds and Thiol-Containing Catalyst System Used Therein."

FIELD OF THE INVENTION

The present invention relates to a process for selectively producing C4 compounds comprising n-butanol and n-butanal, and to the catalyst system used in such process. More particularly, the invention relates to the production of C4 products by the interaction of methanol, hydrogen and carbon monoxide in the presence of a cobalt catalyst, an iodine promoter and a tertiary organo Group VA compound wherein the molar ratio of cobalt to tertiary organo Group VA compounds can be controlled to provide a catalyst system highly selective to the production of C4 products.

DESCRIPTION OF THE PRIOR ART

The reaction of methanol with hydrogen and carbon monoxide to produce ethanol is well known. Generally such processes produce a wide spectrum of compounds in addition to ethanol including other alcohols, as well as ketones, carboxylic acids and the like.

Thus, for example, U.S. Pat. No. 3,285,948 entitled "Halides of Ruthenium and Osmium in Conjunction with Cobalt and Iodine in the Production of Ethanol from Methanol" to G. N. Butter teaches a method for producing alcohols in which any source of cobalt soluble in the reaction medium which will yield a cobalt carbonyl or hydrogen cobalt carbonyl under the reaction conditions can be used. In addition, an iodine promoter is employed, for example, $I_2$, or alkali metal iodides along with a secondary promoter, i.e., ruthenium halide or osmium halide.

Another process is set forth in U.S. Pat. No. 3,248,432 entitled "Process for the Production of Ethyl Alcohol," to A. D. Riley et al which relates to a process for the production of ethyl alcohol by the interaction of methanol, carbon monoxide and hydrogen at elevated temperature and pressure in the presence of a cobalt catalyst and an iodine promoter. Examples of suitable cobalt sources are described as any water-soluble source of cobalt, for example, the cobalt carbonyls, the lower salts of alkanoate cobalt, such as cobalt acetate, cobalt formate, cobalt propionate, and the like.

U.S. Pat. No. 4,133,966 to W. R. Pretzer et al entitled "Selective Formation of Ethanol from Methanol, Hydrogen and Carbon Monoxide" discloses contacting methanol, hydrogen and carbon monoxide with a catalyst system containing cobalt acetylacetonate, a tertiary organo Group VA compound of the Periodic Table, an iodine compound and a ruthenium compound to selectively produce ethanol.

Such processes do not provide significant amounts of C4 products, which are but a minor and incidental by-product of the reactions involved.

SUMMARY OF THE INVENTION

A process and catalyst system have now been discovered for selectively producing n-butanol and n-butanal which process comprises introducing into a reaction zone methanol, hydrogen, carbon monoxide and a catalyst system consisting essentially of a cobalt entity selected from the group consisting of (a) a cobalt carbonyl, (b) a hydrido cobalt carbonyl and (c) a cobalt-containing material convertible to a cobalt carbonyl or a hydrido cobalt carbonyl; an iodine compound; and a tertiary organo Group VA compound of the Periodic Table defined by the formula:

wherein E is a member selected from the group consisting of trivalent arsenic and trivalent antimony and $R_1$, $R_2$ and $R_3$, the same or different, are selected from the group consisting of aryl radicals having from six to 20 carbon atoms and halogen substituted derivatives thereof; and aralkyl and alkaryl radicals having from six to 40 carbon atoms, wherein the molar ratio of the cobalt entity to the arsenic or antimony entity is in the range of about 10:1 to about 1:5, the molar ratio of iodine to cobalt is in the range of about 1:3 to about 1.5:1 when E is arsenic, the molar ratio of iodine to cobalt is in the range of about 1:5 to about 2:1 when E is antimony, subjecting the contents of said reaction zone to an elevated temperature of about 180° C. to about 225° C. and an elevated pressure for a time sufficient to obtain n-butanol and n-butanal. The n-butanol and n-butanal can be then separated and recovered from the reaction mixture by any conventional method including distillation. Surprisingly, it was found that a process for providing a greater selectivity for C4 compounds than for ethanol results by eliminating ruthenium from the catalyst system disclosed in U.S. Pat. No. 4,133,966 to W. R. Pretzer et al and by using only an arsenic or antimony-substituted tertiary organo Group VA compound as defined above wherein $R_1$, $R_2$ and $R_3$ are aryl or halogen-substituted aryl within a specified ratio of iodine to cobalt within a limited temperature range. Thus, the process of the present invention is conducted in the absence of ruthenium.

DESCRIPTION OF THE PREFERRED EMBODIMENTS

The tertiary organo Group VA compound of the present invention has the formula:

wherein E is a member selected from the group consisting of trivalent arsenic and trivalent antimony and $R_1$, $R_2$ and $R_3$, the same or different, are selected from aryl radicals having from six to 20 carbon atoms and halogen derivatives thereof.

The tertiary organo Group VA component as defined herein is essential to the success of the present process in achieving the high degree of selectivity of the reaction in producing a product in which the mole percent $C_4$ components exceed that of ethanol. Suitable tertiary organo Group VA compounds for use in the present process include:

triphenyl arsine,
tri(p-tolyl) arsine,
tri(o-tolyl) arsine,
tri(m-tolyl) arsine,
tri(p-cumyl) arsine,
tri(o-cumyl) arsine,
tri(m-cumyl) arsine,
tri(p-tertiarybutylphenyl) arsine,
tri(m-tertiarybutylphenyl) arsine,
tri(p-normalbutylphenyl) arsine,
tri(m-normalbutylphenyl) arsine,
trinaphthyl arsine,
tri(p-tetradecylphenyl) arsine,
tri(p-biphenyl) arsine,
tri(m-biphenyl) arsine,
tri(o-biphenyl) arsine,
tri(p-cyclohexylphenyl) arsine,
tri(m-cyclohexylphenyl) arsine,
tri(o-cyclohexylphenyl) arsine,
tri(2,4-dimethylphenyl) arsine,
tri(3,5-dimethylphenyl) arsine,
tri(2,3-dimethylphenyl) arsine,
tri(3,4-dimethylphenyl) arsine,
tri(2,5-dimethylphenyl) arsine,
tri(2,6-dimethylphenyl) arsine,
diphenyl (p-tolyl) arsine,
phenyl(m-tolyl) (p-cumyl) arsine,
(2,4-dimethylphenyl) (p-biphenyl) (p-tolyl) arsine,
tri(p-trifluoromethylphenyl) arsine,
tri(pentafluorophenyl) arsine,
tri(2,4,6-trifluorophenyl) arsine,
tri(o-fluorophenyl) arsine,
tri(m-fluorophenyl) arsine,
tri(p-fluorophenyl) arsine,
tri(o-chlorophenyl) arsine,
tri(m-chlorophenyl) arsine,
tri(p-chlorophenyl) arsine,
tri(o-bromophenyl) arsine,
tri(m-bromophenyl) arsine,
tri(p-bromophenyl) arsine,
tri(o-iodophenyl) arsine,
tri(m-iodophenyl) arsine,
tri(p-iodophenyl) arsine,
tri(pentachlorophenyl) arsine,
tri(pentabromophenyl) arsine,
tri(p-trichloromethylphenyl) arsine,
tri(o-trifluoromethylphenyl) arsine,
tri(m-trifluoromethylphenyl) arsine,
(p-trifluoromethylphenyl) diphenyl arsine,
di(p-trifluoromethylphenyl) (p-tolyl) arsine,
triphenyl stibine,
tri(p-tolyl) stibine,
tri(m-tolyl) stibine,
tri(o-tolyl) stibine,
tri(p-cumyl) stibine,
tri(m-cumyl) stibine,
tri(o-cumyl) stibine,
tri(p-tertiarybutylphenyl) stibine,
tri(m-tertiarybutylphenyl) stibine,
tri(o-tertiarybutylphenyl) stibine,
tri(p-normalbutylphenyl) stibine,
tri(m-normalbutylphenyl) stibine,
trinaphthyl stibine,
tri(p-tetradecylphenyl) stibine,
tri(p-biphenyl) stibine,
tri(m-biphenyl) stibine,
tri(o-biphenyl) stibine,
tri(p-cyclohexylphenyl) stibine,
tri(m-cyclohexylphenyl) stibine,
tri(o-cyclohexylphenyl) stibine,
tri(2,4-dimethylphenyl) stibine,
tri(3,5-dimethylphenyl) stibine,
tri(2,3-dimethylphenyl) stibine,
tri(3,4-dimethylphenyl) stibine,
tri(2,5-dimethylphenyl) stibine,
tri(2,6-dimethylphenyl) stibine,
diphenyl(p-tolyl) stibine,
phenyl(m-tolyl)(p-cumyl) stibine,
(2,4-dimethylphenyl)(p-biphenyl)(p-tolyl) stibine,
tri(p-trifluoromethylphenyl) stibine,
tri(pentafluorophenyl) stibine,
tri(2,4,6-trifluorophenyl) stibine,
tri(p-fluorophenyl) stibine,
tri(m-fluorophenyl) stibine,
tri(o-fluorophenyl) stibine,
tri(p-chlorophenyl) stibine,
tri(m-chlorophenyl) stibine,
tri(o-chlorophenyl) stibine,
tri(p-bromophenyl) stibine,
tri(m-bromophenyl) stibine,
tri(o-bromophenyl) stibine,
tri(p-iodophenyl) stibine,
tri(m-iodophenyl) stibine,
tri(o-iodophenyl) stibine,
tri(pentachlorophenyl) stibine,
tri(pentabromophenyl) stibine,
tri(p-trichloromethylphenyl) stibine,
tri(m-trifluoromethylphenyl) stibine,
tri(o-trifluoromethylphenyl) stibine,
(p-trifluoromethylphenyl) diphenyl stibine,
di(p-trifluoromethylphenyl)(p-tolyl) stibine, etc.

The process of the present invention comprises contacting methanol, hydrogen and carbon monoxide with a cobalt entity, an iodine promoter and a tertiary organo Group VA compound at temperatures in the range of about 180° to about 225° C. under reaction conditions for a time sufficient to convert the methanol to the desired n-butanol and n-butanal. Although hydrogen and carbon monoxide are employed herein for reaction with methanol to produce the $C_4$ products, it is understood that any combination of compounds that will form hydrogen and carbon monoxide in the reaction zone can also be used. Thus, compounds of reaction mixtures which give rise to the formation of carbon monoxide and hydrogen under the reaction conditions defined herein can be used instead of mixtures comprising carbon monoxide and hydrogen which are used in the preferred embodiments of this invention. For example, mixtures of hydrogen and carbon monoxide, water and carbon monoxide, etc., can be employed.

The mixture of hydrogen and carbon monoxide used herein can be produced from any source containing carbon and hydrogen. Two types of reactions, for example, can be used for the production of synthesis gas, i.e., partial oxidation and steam reforming. Steam reforming is the more important process when natural gas (methane) is the hydrogen-carbon source. Partial oxidation is used primarily for heavy fuel and residual oil.

The relative amounts of carbon monoxide and hydrogen employed can be varied over a wide range. However, in general, the molar ratio range of carbon monoxide to hydrogen is from about 1:10 to about 10:1, especially from about 1:3 to about 3:1. However, conventional synthesis gas (mixtures of carbon monoxide and hydrogen) with a molar ratio of about 1:1 is convenient and satisfactory for the process of the present invention. It is to be noted that molar ratios outside the aforestated ratio ranges can be employed.

The cobalt compound used in the catalyst system of the present invention can be a cobalt carbonyl, a hydrido cobalt carbonyl or a cobalt-containing material convertible to a cobalt carbonyl or a hydrido cobalt carbonyl. The term "cobalt carbonyl" as used in this application is a compound containing only cobalt and carbon monoxide, such as $Co_2(CO)_8$ or $Co_4(CO)_{12}$. The term "hydrido cobalt carbonyl" as used herein is a compound containing only cobalt, carbon monoxide and hydrogen, such as $HCo(CO)_4$. The expression "cobalt-containing material convertible to a cobalt carbonyl or a hydrido cobalt carbonyl" includes any material which when mixed with hexane and then subjected to 4000 pounds per square inch gauge (27.6 MPa) in an atmosphere containing hydrogen and carbon monoxide in a ratio of 1:1 at 150° C. to 200° C. for a period of three hours will result in the formation of a cobalt carbonyl, a hydrido cobalt carbonyl or mixtures thereof.

Specific examples of such cobalt-containing material convertible to a cobalt carbonyl or a hydrido cobalt carbonyl include cobalt acetylacetonate, cobalt(II) sulfate, cobalt oxide ($Co_3O_4$), cobalt(II) tetrafluoroborate, cobalt(II) acetate, cobalt(II) oxalate, cobalt(II) propionate, cobalt(II) octoate, cobalt(II) butyrate, cobalt(II) benzoate, cobalt(II) valerate, cobalt(II) formate, cobalt(II) cyclohexanebutyrate, cobalt(II) 2-ethylhexaoate, cobalt(II) gluconate, cobalt(II) lactate, cobalt(II) naphthenate, cobalt(II) oleate and cobalt(II) citrate.

Any source of iodine which is capable of disassociating, that is, ionizing to form free iodide ions in the reaction medium, can be used as a promoter in the catalyst system used in the process of the present invention. Illustrative examples of iodine compounds suitable for use herein include iodine, potassium iodide, calcium iodide, sodium iodide, lithium iodide, hydrogen iodide, methyl iodide, ethyl iodide, mixtures thereof and the like.

The molar ratio of iodine to cobalt utilized is critical in order to achieve the high degree of selectivity to $C_4$ compounds. Thus, when a trivalent arsenic modifier is used, the molar ratio of iodine to cobalt must be in the range of about 1:3 to about 1.5:1, preferably about 1:2 to about 1:1. Likewise, when the modifier is trivalent antimony, the molar ratio of iodine to cobalt must be in the range of about 1:5 to about 2:1, preferably from about 1:4 to about 1.5:1. The aforesaid ratios are based upon elemental iodine and cobalt.

The ratio of the cobalt entity to the tertiary organo Group VA compound used in the reaction is vital in order to achieve large amounts of $C_4$ product and correspondingly reduce the ethanol yield. Thus, in order to provide a highly selective catalyst system, the cobalt catalyst and the tertiary organo Group VA compound are utilized in molar ratios, based on the elements cobalt and arsenic or antimony, in a ratio of cobalt to arsenic or antimony of from about 10:1 to about 1:5. Based on the weight of methanol introduced into the system, the weight percent of combined cobalt, arsenic or antimony, and iodine can range from about 0.01 to about 10 percent, preferably from about 0.1 to about 5 percent.

The process can be carried out either in a batch operation or by passing the reactants continuously through the reactor. In each case the reactor is provided with agitation means and the pressure is maintained therein by the addition of hydrogen and carbon monoxide as required. In order to facilitate introduction of the cobalt, arsenic or antimony, and iodine entities into the reaction zone and/or to facilitate recovery of the components of the reaction herein, they can be dissolved in an inert solvent, such as ethylene glycol, diethylene glycol monomethyl ether, acetone, sulfolanes, lactones etc.

In the reaction zone the reactants are maintained at elevated temperature and elevated pressure for a time sufficient to convert the methanol to a product in which the mole percent of the combined $C_4$ products (n-butanol and n-butanal) exceeds that of ethanol. Temperatures which are suitable for use in the present process are those temperatures from about 180° C. to about 225° C., preferably from about 190° C. to about 215° C. Pressures which are suitable for use in the present process generally are in the range of about 1000 to about 6000 pounds per square inch gauge (about 6.83 to about 40.98 MPa), preferably about 2000 to about 5000 pounds per square inch gauge (about 13.66 to about 34.15 MPa). The reaction is conducted for a time period sufficient to convert methanol to $C_4$ products, normally from about 0.5 hour to about 10 hours, preferably from about one to about five hours.

Recovery of the $C_4$ products from the reaction product can be effected in any convenient or conventional manner, for example, by distillation. At ambient pressure and about 21° C., the components will distill off in the following sequence for the desired recovery of the $C_4$ products and any other compounds for which recovery is desired: dimethyl ether, acetaldehyde, methyl acetate, methanol, n-butanal, ethanol and n-butanol.

The following examples illustrate the process and catalyst system of the present invention. The percentages are by weight.

EXAMPLES I-VI

Six millimoles of cobalt acetylacetonate, 0.38 grams of iodine and 100 milliliters of methanol were charged into a 300 cc. stainless steel autoclave. The reactor was next purged twice with nitrogen gas and then pressured with synthesis gas ($H_2$:CO=1) to a pressure of about 1000 pounds per square inch gauge (6.83 MPa) lower than the desired working pressure. The system was then heated to a temperature of about 200° C. and the pressure was adjusted to a working pressure of about 4000 pounds per square inch gauge (27.6 MPa). The reaction was allowed to proceed for approximately three hours, after which the reactor was cooled by an internal cooling coil to about −75° C. The reactor was vented through a dry gas meter and a gas sample was taken for a mass spectral analysis and the liquid product was analyzed using a Model 900 Perkin-Elmer gas chromatograph utilizing a 16-foot (4.88 meters)×⅛ inch (0.32 centimeter) stainless steel column wherein 8 feet (2.44 meters) of the column was packed with 80/100 mesh Poropak Q and the other 8 feet (2.44 meters) was packed with 80/100 mesh Poropak R. Poropak Q and Poropak R are polyvinyl benzene-type resins which are marketed commercially by Waters Associates, a corporation located in Milford, Mass. The gas chromatograph was programmed to increase from 40° C. to 190° C. at a rate of 32° C./minute and with a helium flow rate of 30 cc/minute.

The aforesaid procedure was repeated except that six millimoles of an arsenic or antimony compound was charged to the autoclave along with the cobalt acetylacetonate, iodine and methanol, in separate runs. The results for each of the foregoing runs are set forth in Table I:

TABLE I

| Example No. | Arsenic or Antimony | Percent MeOH Conv. (a) | Mole Percent Selectivity | | | | | | | | |
|---|---|---|---|---|---|---|---|---|---|---|---|
| | | | Me$_2$O (b) | AcH (c) | EtOH (d) | MeOAc (e) | MeCH(OMe)$_2$ (f) | n-PrCHO (g) | n-BuOH (h) | Other (i) | C$_4$ (j) |
| I | None | 70.9 | 6.1 | 21.8 | 45.2 | 17.3 | <1 | 4.2 | <1 | 5.4 | 4.2 |
| II | Methyl Diphenyl Arsine | 66.3 | 3.6 | 46.8 | 19.6 | 16.8 | <1 | 13.1 | <1 | <1 | 13.1 |
| III | Triphenyl Arsine | 56.0 | 7.3 | 21.6 | 16.0 | 22.5 | <1 | 17.8 | 12.8 | 2.0 | 30.6 |
| IV | Triethyl Arsine | 60.7 | 2.4 | 24.1 | 48.0 | 17.9 | <1 | 3.8 | <1 | 3.8 | 3.8 |
| V | Triphenyl Stibine | 38.6 | 23.6 | 31.2 | 3.8 | 13.6 | <1 | 4.0 | 21.9 | 1.9 | 25.9 |
| VI | Tri-n-butyl Stibine | 32.6 | 7.6 | 26.1 | 27.8 | 16.9 | <1 | 11.0 | 2.2 | 8.4 | 13.3 |

(a) MeOH = Methanol
(b) Me$_2$O = Dimethyl Ether
(c) AcH = Acetaldehyde
(d) EtOH = Ethanol
(e) MeOAc = Methyl Acetate
(f) MeCH(OMe)$_2$ = Dimethyl Acetal
(g) n-PrCHO = n-butanal
(h) n-BuOH = n-butanol
(i) Other = Mixtures of ethyl acetate, methyl formate, propanols, propionaldehyde and methane.
(j) C$_4$ = Total C$_4$ products The data in Table I show the criticality of using triaryl substituted arsines and stibines, since only in Examples III and V did the selectivity to C$_4$ products exceed the selectivity to ethanol. The use of a di-aryl substituted arsine as in Example II did not provide selectivity to C$_4$ products exceeding selectivity to ethanol.

EXAMPLES VII-XIII

The procedure of the foregoing examples is repeated using six millimoles of triphenyl arsine, six millimoles of cobalt acetylacetonate and varying amounts of iodine. The results are shown in Table II:

TABLE II

| Example No. | I:Co (Molar Ratio) | Percent MeOH Conv. (a) | Mole Percent Selectivity | | | | | | | | | C$_4$ Yield (k) |
|---|---|---|---|---|---|---|---|---|---|---|---|---|
| | | | Me$_2$O (b) | AcH (c) | EtOH (d) | MeOAc (e) | MeCH(OMe)$_2$ (f) | n-PrCHO (g) | n-BuOH (h) | Other (i) | C$_4$ (j) | |
| VII | 0 | 7.7 | 28.1 | <1 | 41.7 | 30.2 | <1 | <1 | <1 | <1 | <1 | — |
| VIII | 1:8 | 40.6 | 7.6 | 49.6 | 19.4 | 17.1 | <1 | 5.1 | <1 | 1.2 | 5.1 | 2.0 |
| IX | 1:4 | 60.5 | 5.4 | 56.5 | 16.7 | 13.1 | <1 | 6.3 | <1 | 2.0 | 6.3 | 3.8 |
| X | 1:2 | 56.0 | 7.3 | 21.6 | 16.0 | 22.5 | <1 | 17.8 | 12.8 | 2.0 | 30.6 | 17.1 |
| XI | 1:1 | 56.7 | 7.4 | 21.6 | 16.1 | 23.2 | <1 | 17.6 | 10.1 | 4.0 | 27.7 | 15.7 |
| XII | 2:1 | 49.4 | 9.4 | 21.7 | 17.7 | 36.3 | <1 | 14.2 | <1 | 0.7 | 14.2 | 7.0 |
| XIII | 5:1 | 66.2 | 67.1 | 7.4 | 1.4 | 12.7 | <1 | 3.2 | 6.7 | 1.5 | 9.9 | 6.6 |

(a) MeOH = Methanol
(b) Me$_2$O = Dimethyl Ether
(c) AcH = Acetaldehyde
(d) EtOH = Ethanol
(e) MeOAc = Methyl Acetate
(f) MeCH(OMe)$_2$ = Dimethyl Acetal
(g) n-PrCHO = n-butanal
(h) n-BuOH = n-butanol
(i) Other = Mixtures of ethyl acetate, methyl formate, propanols, propionaldehyde and methane.
(j) C$_4$ = Total C$_4$ products
(k) C$_4$ Yield = Total C$_4$ product yield The data in Table II show the criticality of using an iodine/cobalt molar ratio (based upon elemental iodine and cobalt) in the range of 1:3 to 1.5:1 with an arsine for achieving a selectivity to C4 products which exceeds selectivity to ethanol. Thus, in Examples X and XI using an iodine/cobalt molar ratio of 1:2 and 1:1, respectively, the selectivity to C4 products obtained was 30.6 and 27.7 mole percent, respectively, as compared with selectivity to ethanol of about 16 mole percent in each case. In the remaining examples, the iodine/cobalt ratio was outside the critical range, and the selectivity to ethanol exceeded that to C4 products.

EXAMPLES XIV–XVIII

The procedure of Examples VII–XIII was repeated, except that triphenyl stibine was substituted for triphenyl arsine. The results are set forth in Table III:

EXAMPLES XIX–XXII

The procedure of Examples I–VI was repeated, except that the arsenic or antimony compound used was triphenyl arsine and that the temperature of the reaction was varied for each run. The results for each of the foregoing runs are set forth in Table IV:

TABLE IV

| | | | Mole Percent Selectivity | | | | | | | | |
|---|---|---|---|---|---|---|---|---|---|---|---|
| Example No. | Temperature (°C.) | Percent MeOH Conv. (a) | Me$_2$O (b) | AcH (c) | EtOH (d) | MeOAc (e) | MeCH(OMe)$_2$ (f) | n-PrCHO (g) | n-BuOH (h) | Other (i) | C$_4$ (j) |
| XIX | 150 | 0.0 | — | — | — | — | — | — | — | — | — |
| XX | 175 | 42.6 | 2.4 | 58.2 | 10.3 | 18.3 | <1 | 0.5 | <1 | 10.3 | 0.5 |
| XXI | 200 | 56.0 | 7.3 | 21.6 | 16.0 | 22.5 | <1 | 17.8 | 12.8 | 2.0 | 30.6 |
| XXII | 225 | 41.3 | 35.6 | 46.2 | 2.4 | 6.9 | <1 | 3.5 | 3.2 | 2.2 | 6.7 |

(a) MeOH = Methanol
(b) Me$_2$O = Dimethyl Ether
(c) AcH = Acetaldehyde
(d) EtOH = Ethanol
(e) MeOAc = Methyl Acetate
(f) MeCH(OMe)$_2$ = Dimethyl Acetal
(g) n-PrCHO = n-butanal
(h) n-BuOH = n-butanol
(i) Other = Mixtures of ethyl acetate, methyl formate, propanols, propionaldehyde and methane.
(j) C$_4$ = Total C$_4$ products The data in Table IV show the criticality of using a reaction temperature in the range of about 180° C. to about 225° C. for achieving a selectivity to C4 products which exceeds selectivity to ethanol. Thus, the selectivity to C4 products at 175° C. was only 0.5 mole percent (Example XX) but increased dramatically to 30.6 mole percent (Example XXI) by increasing the temperature to 200° C. When the temperature is further increased to 225° C. (Example XXII), the C4 selectivity drops to 6.7 mole percent, but still exceeds selectivity to ethanol.

TABLE III

| | | | Mole Percent Selectivity | | | | | | | | | |
|---|---|---|---|---|---|---|---|---|---|---|---|---|
| Example No. | I:Co (Molar Ratio) | Percent MeOH Conv. (a) | Me$_2$O (b) | AcH (c) | EtOH (d) | MeOAc (e) | MeCH(OMe)$_2$ (f) | n-PrCHO (g) | n-BuOH (h) | Other (i) | C$_4$ (j) | C$_4$ Yield (k) |
| XIV | 1:8 | 5.6 | 22.0 | — | — | 53.7 | — | — | — | 24.3 | — | — |
| XV | 1:4 | 28.7 | 22.4 | 33.0 | 5.2 | 6.4 | <1 | <1 | 21.6 | 11.4 | 21.6 | 6.2 |
| XVI | 1:2 | 38.6 | 23.6 | 31.2 | 3.8 | 13.6 | <1 | 4.0 | 21.9 | 1.9 | 25.9 | 10.0 |
| XVII | 1:1 | 37.5 | 30.7 | 17.2 | 7.7 | 18.4 | <1 | 5.5 | 17.7 | 2.8 | 23.2 | 8.7 |
| XVIII | 3:1 | 40.0 | 59.8 | 10.9 | 2.7 | 17.2 | <1 | 4.6 | 4.8 | <1 | 9.4 | 3.8 |

(a) MeOH = Methanol
(b) Me$_2$O = Dimethyl Ether
(c) AcH = Acetaldehyde
(d) EtOH = Ethanol
(e) MeOAc = Methyl Acetate
(f) MeCH(OMe)$_2$ = Dimethyl Acetal
(g) n-PrCHO = n-butanal
(h) n-BuOH = n-butanol
(i) Other = Mixtures of ethyl acetate, methyl formate, propanols, propionaldehyde and methane.
(j) C$_4$ = Total C$_4$ products
(k) C$_4$ Yield = Total C$_4$ product yield The data in Table III show the criticality of using a ratio of iodine/cobalt in the range of 1:5 to 2:1 with a stibine. Thus, the examples show an iodine/cobalt ratio of 1:2 (Example XV) produced a C4 selectivity of 21.6 mole percent; a ratio of 1:2 (Example XVI) produced a 25.9 mole percent selectivity to C4 products; and a ratio of 1:1 (Example XVII) resulted in a C4 selectivity of 23.2 mole percent. In each such instance, the C4 selectivity exceeded the ethanol selectivity.

EXAMPLES XXIII–XXIX

The procedure of Examples I–VI was repeated, except that six millimoles of a cobalt entity, six millimoles of triphenyl arsine and 0.38 grams of iodine were charged to the autoclave along with the methanol in separate runs. The results for each of the foregoing runs are set forth in Table V:

TABLE V

| | | Percent | Mole Percent Selectivity | | | | | | | | |
|---|---|---|---|---|---|---|---|---|---|---|---|
| Example No. | Cobalt Entity | MeOH Conv. (a) | Me$_2$O (b) | AcH (c) | EtOH (d) | MeOAc (e) | MeCH(OMe)$_2$ (f) | n-PrCHO (g) | n-BuOH (h) | Other (i) | C$_4$ (j) |
| XXIII | cobalt acetyl- | | | | | | | | | | |

TABLE V-continued

| Example No. | Cobalt Entity | Percent MeOH Conv. (a) | Mole Percent Selectivity | | | | | | | | |
|---|---|---|---|---|---|---|---|---|---|---|---|
| | | | Me$_2$O (b) | AcH (c) | EtOH (d) | MeOAc (e) | MeCH(OMe)$_2$ (f) | n-PrCHO (g) | n-BuOH (h) | Other (i) | C$_4$ (j) |
| XIV | acetonate cobalt | 32.0 | 5.6 | 28.0 | 11.7 | 19.1 | 10 | 14.6 | 10 | 10 | 24.6 |
| XXV | acetate cobalt | 36.2 | 8.6 | 44.3 | 9.4 | 16.3 | <1 | 9.9 | 11.4 | <1 | 21.3 |
| XXVI | oxalate cobalt | 41.9 | 14.5 | 21.2 | 6.2 | 16.9 | 12.7 | 4.4 | 24.2 | <1 | 28.6 |
| XXVII | benzoate cobalt | 36.5 | 9.6 | 33.6 | 11.0 | 18.5 | <1 | 9.9 | 17.4 | <1 | 27.3 |
| XXVIII | sulfate cobalt | 38.8 | 15.8 | 25.4 | 4.6 | 15.8 | 0.1 | 6.5 | 31.8 | <1 | 38.3 |
| XXIX | carbonyl cobalt | 33.5 | 11.5 | 35.1 | 12.4 | 16.3 | <1 | 11.5 | 9.7 | 1.5 | 21.2 |
| | oxide | 42.2 | 9.7 | 45.2 | 13.6 | 12.3 | <1 | 8.7 | 7.9 | 2.6 | 16.6 |

(a) MeOH = Methanol
(b) Me$_2$O = Dimethyl Ether
(c) AcH = Acetaldehyde
(d) EtOH = Ethanol
(e) MeOAc = Methyl Acetate
(f) MeCH(OMe)$_2$ = Dimethyl Acetal
(g) n-PrCHO = n-butanal
(h) n-BuOH = n-butanol
(i) Other = Mixtures of ethyl acetate, methyl formate, propanols, propionaldehyde and methane.
(j) C$_4$ = Total C$_4$ products The data of Table V show that the particular cobalt compound utilized can be varied and still achieve a high C$_4$ selectivity. However, the highest C$_4$ selectivity was achieved using cobalt sulfate (Example XXVIII). The selectivity to C$_4$ products ranged from 38.3 mole percent (Example XXVII) for cobalt sulfate to 16.6 mole percent (Example XXIX) for cobalt oxide, which exceeded the selectivity to ethanol which was 4.6 mole percent and 13.6 mole percent, respectively.

EXAMPLES XXX–XXXIII

The foregoing procedure was repeated, except that six millimoles of a cobalt entity, three millimoles of an iodine were charged to the autoclave along with six millimoles of triphenyl arsine and the methanol in separate runs. The results for each of the foregoing runs are as set forth in Table VI:

TABLE VI

| Example No. | Catalyst System | Percent MeOH Conv. (a) | Mole Percent Selectivity | | | | | | | | |
|---|---|---|---|---|---|---|---|---|---|---|---|
| | | | Me$_2$O (b) | AcH (c) | EtOH (d) | MeOAc (e) | MeCH(OMe)$_2$ (f) | n-PrCHO (g) | n-BuOH (h) | Other (i) | C$_4$ (j) |
| XXX | Cobalt acetylacetonate + iodine + triphenyl arsine | 32.0 | 5.6 | 28.0 | 11.7 | 19.1 | 10 | 14.6 | 10 | 1.0 | 24.6 |
| XXXI | Cobaltous acetate + zinc iodide + triphenyl arsine | 34.0 | 5.9 | 33.5 | 8.3 | 13.5 | 4.8 | 6.3 | 4.0 | 23.7 | 10.3 |
| XXXII | Cobalt acetylacetonate + methyl iodide + triphenyl arsine | 41.1 | 8.6 | 42.4 | 10.1 | 11.6 | <1 | 10.4 | 14.7 | 2.2 | 25.1 |
| XXXIII | Cobalt acetylacetonate + hydrogen iodide + triphenyl arsine | 38.6 | 7.5 | 41.7 | 10.6 | 12.8 | <1 | 10.3 | 15.0 | 2.1 | 25.3 |

(a) MeOH = Methanol
(b) Me$_2$O = Dimethyl Ether
(c) AcH = Acetaldehyde
(d) EtOH = Ethanol
(e) MeOAc = Methyl Acetate
(f) MeCH(OMe)$_2$ = Dimethyl Acetal
(g) n-PrCHO = n-butanal
(h) n-BuOH = n-butanol
(i) Other = Mixtures of ethyl acetate, methyl formate, propanols, propionaldehyde and methane.
(j) C$_4$ = Total C$_4$ products The data in Table VI show that the type of iodine and cobalt compounds utilized can be varied without reducing the selectivity to C$_4$ products below that to ethanol. Different iodines produce no significant difference to C$_4$ selectivity as shown in Example XXX (iodine) with a selectivity of 24.6 mole percent, Example XXXII (methyl iodide) with a selectivity of 25.1 mole percent and Example XXXIII (hydrogen iodide) with a selectivity of 25.3 mole percent.

EXAMPLES XXXIV–XXXVII

The foregoing procedure was repeated, except that six millimoles of a cobalt entity and varying amounts of iodine were charged to the autoclave with six millimoles of triphenyl arsine and the methanol in separate runs. The results for each run are as set forth in Table VII:

TABLE VII

| Example No. | I:Co (Molar Ratio) | Cobalt Entity | Percent MeOH Conv. (a) | Mole Percent Selectivity | | | | | | | | |
|---|---|---|---|---|---|---|---|---|---|---|---|---|
| | | | | Me$_2$O (b) | AcH (c) | EtOH (d) | MeOAc (e) | MeCH(OMe)$_2$ (f) | n-PrCHO (g) | n-BuOH (h) | Other (i) | C$_4$ (j) |
| XXXIV | 1:2 | Cobalt Carbonyl | 33.5 | 11.5 | 35.1 | 12.4 | 16.3 | <1 | 11.5 | 9.7 | 1.5 | 21.2 |
| XXXV | 1:2 | Cobalt Oxalate | 36.2 | 8.6 | 44.3 | 9.4 | 16.3 | <1 | 9.9 | 11.4 | <1 | 21.3 |
| XXXVI | 2.5:1 | Cobalt Carbonyl | 50.5 | 20.3 | 16.9 | 18.0 | 26.1 | <1 | 8.3 | 8.8 | 1.6 | 17.1 |
| XXXVII | 2.5:1 | Cobalt Oxalate | 52.3 | 31.0 | 14.7 | 13.9 | 25.3 | <1 | 6.6 | 8.4 | <1 | 15.0 |

(a) MeOH = Methanol
(b) Me$_2$O = Dimethyl Ether
(c) AcH = Acetaldehyde
(d) EtOH = Ethanol
(e) MeOAc = Methyl Acetate
(f) MeCH(OMe)$_2$ = Dimethyl Acetal
(g) n-PrCHO = n-butanal
(h) n-BuOH = n-butanol
(i) Other = Mixtures of ethyl acetate, methyl formate, propanols, propionaldehyde and methane.
(j) C$_4$ = Total C$_4$ products The data of Table VII further demonstrate the criticality of using an iodine/cobalt molar ratio in the range of about 1:3 to 1.5:1 for an arsine compound for achieving a selectivity to C$_4$ products which exceeds selectivity to ethanol. Thus, Examples XXXIV and XXXV show that using an iodine/cobalt ratio of 1:2 produced a C$_4$ selectivity of 21.2 mole percent (Example XXXIV) using a cobalt carbonyl and 21.3 mole percent (Example XXXV) using a cobalt oxalate.

Obviously, many modifications and variations of the invention, as hereinabove set forth, can be made without departing from the spirit and scope thereof, and therefore only such limitations should be imposed as are indicated in the appended claims.

We claim:

1. A process for selectively producing n-butanol and n-butanal, which comprises reacting methanol, hydrogen and carbon monoxide in the presence of a catalyst system which consists essentially of (a) a cobalt entity selected from the group consisting of a cobalt carbonyl, a hydrido cobalt carbonyl and a cobalt-containing material convertible to a cobalt carbonyl or a hydrido cobalt carbonyl, (b) an iodine promoter and (c) a tertiary organo compound defined by the formula:

wherein E is a member selected from the group consisting of trivalent arsenic and trivalent antimony and R$_1$, R$_2$ and R$_3$, the same or different, are selected from the group consisting of aryl radicals having from six to 20 carbon atoms and halogen substituted derivatives thereof, and aralkyl and alkaryl radicals having from six to 40 carbon atoms, wherein the molar ratio of the cobalt entity to the arsenic or antimony entity is in the range of about 10:1 to about 1:5, the molar ratio of iodine to cobalt is in the range of about 1:3 to about 1.5:1 when E is arsenic, the molar ratio of iodine to cobalt is in the range of about 1:5 to about 2:1 when E is antimony, subjecting the contents of said reaction zone to an elevated temperature of about 180° C. to about 225° C. and an elevated pressure for a time sufficient to obtain n-butanol and n-butanal.

2. The process of claim 1 wherein R$_1$, R$_2$ and R$_3$ are either alike or different members selected from the group consisting of aryl radicals having from six to 10 carbon atoms and halogen substituted derivatives thereof.

3. The process of claim 1 wherein the tertiary organo compound is triphenyl arsine or triphenyl stibine.

4. The process of claim 3 wherein the tertiary organo compound is triphenyl arsine.

5. The process of claim 3 wherein the tertiary organo compound is triphenyl stibine.

6. The process of claim 1 wherein the cobalt entity is cobalt acetylacetonate.

7. The process of claim 1 wherein the cobalt entity is cobalt acetate.

8. The process of claim 1 wherein the cobalt entity is cobalt oxide.

9. The process of claim 1 wherein the cobalt entity is cobalt sulfate.

10. The process of claim 1 wherein the cobalt entity is cobalt carbonyl.

11. The process of claim 1 wherein the cobalt entity is cobalt oxalate.

12. The process of claim 1 wherein the cobalt entity is cobalt benzoate.

13. The process of claim 1 wherein the iodine compound is a member selected from the group consisting of iodine, potassium iodide, calcium iodide, sodium iodide, lithium iodide, hydrogen iodide, methyl iodide and ethyl iodide, or mixtures thereof.

14. The process of claim 13 wherein the iodine promoter is iodine.

15. The process of claim 13 wherein the iodine promoter is zinc iodide.

16. The process of claim 13 wherein the iodine promoter is methyl iodide.

17. The process of claim 13 wherein the iodine promoter is hydrogen iodide.

18. The process of claim 1 wherein the weight percent of the combined cobalt, arsenic or antimony and iodine is in the range of about 0.01 to about 10 percent.

19. The process of claim 18 wherein the weight percent of the combined cobalt, arsenic or antimony and iodine is in the range of about 0.1 to about 5 percent.

20. The process of claim 1 wherein the reaction temperature is about 190° C. to about 215° C.

21. The process of claim 1 wherein the reaction pressure is about 1000 pounds per square inch gauge to about 6000 pounds per square inch gauge.

22. The process of claim 21 wherein the reaction pressure is about 2000 pounds per square inch gauge to about 5000 pounds per square inch gauge.

23. The process of claim 1 wherein the reaction time is about 0.5 to about 10 hours.

24. The process of claim 23 wherein the reaction time is about 1 to about 5 hours.

25. The process of claim 1 wherein the molar ratios of carbon monoxide to hydrogen are about 1:10 to about 10:1.

26. The process of claim 25 wherein the molar ratios of carbon monoxide to hydrogen are about 1:3 to about 3:1.

* * * * *